US007590443B2

(12) United States Patent
Bharmi

(10) Patent No.: US 7,590,443 B2
(45) Date of Patent: Sep. 15, 2009

(54) SYSTEM AND METHOD FOR DETECTING HYPOGLYCEMIA BASED ON A PACED DEPOLARIZATION INTEGRAL USING AN IMPLANTABLE MEDICAL DEVICE

(75) Inventor: Rupinder Bharmi, Stevenson Ranch, CA (US)

(73) Assignee: Pacesetter, Inc, Sylmar, CA (US)

( * ) Notice: Subject to any disclaimer, the term of this patent is extended or adjusted under 35 U.S.C. 154(b) by 609 days.

(21) Appl. No.: 11/117,624

(22) Filed: Apr. 27, 2005

(65) Prior Publication Data
US 2006/0247685 A1 Nov. 2, 2006

(51) Int. Cl.
A61B 5/0205 (2006.01)
(52) U.S. Cl. ..................... 600/509; 600/365
(58) Field of Classification Search ........... 600/365, 600/509
See application file for complete search history.

(56) References Cited

U.S. PATENT DOCUMENTS

| | | | |
|---|---|---|---|
| 4,731,051 A | 3/1988 | Fischell | |
| 4,759,366 A | 7/1988 | Callaghan | 128/419 PG |
| 4,947,845 A | 8/1990 | Davis | |
| 5,113,869 A | 5/1992 | Nappholz et al. | |
| 5,135,004 A | 8/1992 | Adams et al. | |
| 5,148,812 A | 9/1992 | Verrier et al. | |
| 5,199,428 A | 4/1993 | Obel et al. | |
| 5,203,326 A | 4/1993 | Collins | |
| 5,313,953 A | 5/1994 | Yomtov et al. | |
| 5,328,460 A | 7/1994 | Lord et al. | |
| 5,365,426 A | 11/1994 | Siegel et al. | |

(Continued)

FOREIGN PATENT DOCUMENTS

EP 0472411 A1 2/1990

(Continued)

OTHER PUBLICATIONS

Bruce M. Steinhaus and Tibor A. Nappholz, "The Information Content of the Cardiac Electrogram at the Stimulus Site," Annual International Conference of the IEEE Engineering in Medicine and Biology Society, vol. 12, No. 2, 1990.

(Continued)

Primary Examiner—Carl H Layno
Assistant Examiner—Eric D Bertram

(57) ABSTRACT

Techniques are provided for use with an implantable medical device such as a pacemaker or implantable cardioverter/defibrillator (ICD) for predicting and detecting hypoglycemia. In one example, the device tracks changes in a paced depolarization integral (PDI). A significant increase in PDI over a relatively short period of time indicates the onset of hypoglycemia (this can also be confirmed with QT changes). Upon detection of hypoglycemia, appropriate warning signals are generated to alert the patient. Certain therapies automatically provided by the implantable device may also be controlled in response to hypoglycemia. For example, if the patient is an insulin-dependent diabetic and the implantable device is equipped with an insulin pump capable of delivering insulin directly into the bloodstream, insulin delivery is automatically suspended until blood glucose levels return to acceptable levels. If the device is an ICD, it may be controlled to begin charging defibrillation capacitors upon detection of hypoglycemia so as to permit prompt delivery of a defibrillation shock, which may be needed if hypoglycemia triggers ventricular fibrillation. The detection techniques may be used in conjunction with other hypoglycemia detection techniques to improve detection specificity.

16 Claims, 8 Drawing Sheets

U.S. PATENT DOCUMENTS

| | | |
|---|---|---|
| 5,400,795 A | 3/1995 | Murphy et al. |
| 5,425,749 A | 6/1995 | Adams |
| 5,520,191 A | 5/1996 | Karlsson et al. |
| 5,720,295 A | 2/1998 | Greenhut et al. |
| 5,741,211 A * | 4/1998 | Renirie et al. ............... 600/300 |
| 5,785,660 A | 7/1998 | van Lake et al. |
| 5,792,065 A | 8/1998 | Xue |
| 5,891,047 A | 4/1999 | Lander et al. |
| 5,960,797 A | 10/1999 | Kramer et al. |
| 6,016,443 A | 1/2000 | Ekwall et al. |
| 6,021,350 A | 2/2000 | Mathson |
| 6,038,469 A | 3/2000 | Karlsson et al. |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,249,705 B1 | 6/2001 | Snell |
| 6,256,538 B1 | 7/2001 | Ekwall |
| 6,264,606 B1 | 7/2001 | Ekwall et al. |
| 6,272,379 B1 | 8/2001 | Fischell et al. |
| 6,361,503 B1 | 3/2002 | Starobin et al. |
| 6,377,852 B1 | 4/2002 | Bornzin et al. |
| 6,381,493 B1 | 4/2002 | Stadler et al. |
| 6,501,983 B1 | 12/2002 | Natarajan et al. |
| 6,572,542 B1 | 6/2003 | Houben et al. ............... 600/300 |
| 6,622,045 B2 | 9/2003 | Snell et al. ................... 607/30 |
| 6,731,985 B2 | 5/2004 | Poore et al. ................... 607/28 |
| 7,010,345 B2 | 3/2006 | Hill et al. |
| 7,016,720 B2 | 3/2006 | Kroll |
| 7,029,443 B2 | 4/2006 | Kroll |
| 7,076,300 B1 | 7/2006 | Kroll et al. |
| 7,096,064 B2 | 8/2006 | Deno et al. |
| 7,103,412 B1 | 9/2006 | Kroll |
| 7,142,911 B2 | 11/2006 | Boileau et al. |
| 7,272,436 B2 * | 9/2007 | Gill et al. .................... 600/513 |
| 7,297,114 B2 * | 11/2007 | Gill et al. .................... 600/365 |
| 7,435,221 B1 * | 10/2008 | Bharmi et al. ............... 600/484 |
| 2002/0143266 A1 | 10/2002 | Bock |
| 2002/0143372 A1 | 10/2002 | Snell et al. |
| 2004/0077962 A1 | 4/2004 | Kroll .......................... 600/513 |
| 2004/0078065 A1 * | 4/2004 | Kroll .......................... 607/60 |
| 2004/0138716 A1 | 7/2004 | Kon et al. |
| 2004/0249420 A1 | 12/2004 | Olson et al. |
| 2005/0288725 A1 | 12/2005 | Hettrick et al. |
| 2006/0167365 A1 | 7/2006 | Bharmi |
| 2006/0167517 A1 * | 7/2006 | Gill et al. .................... 607/25 |
| 2006/0167518 A1 | 7/2006 | Gill et al. |
| 2006/0167519 A1 | 7/2006 | Gill et al. |
| 2006/0247685 A1 | 11/2006 | Bharmi |

FOREIGN PATENT DOCUMENTS

| | | |
|---|---|---|
| EP | 0867146 A1 | 9/1998 |
| EP | 0867146 A1 | 2/2004 |
| EP | 1419731 A1 | 5/2004 |
| EP | 0939602 B1 | 9/2004 |
| EP | 1419731 B1 | 12/2007 |
| WO | 97/15227 | 5/1997 |
| WO | 2006/081336 A2 | 8/2006 |

OTHER PUBLICATIONS

Blendea, Mihaela C., MD, PhD, et al, "Heart Disease in Diabetic Patients," Current Diabetes Reports. 2003;3:223-229.

Harris, ND et al, "Can Changes in QT Interval be used to Predict the Onset of Hypoglycemia in Type 1 Diabetes?" Computers in Cardiology 2000;27:375-378.

Landstedt-Hallin, L. et al., "Increased QT dispersion during hypoglycaemia in patients with type 2 diabetes mellitus," J Intern Med. 1999;246:299-307.

Malmberg, Klas for the DIGAMI Study Group, "Prospective randomised study of Intensive insulin treatment on long-term survival after acute myocardial infarction in patients with diabetes mellitus", BMJ. May 24,1997;314:1512-1515.

Markel, A., Hypoglycaemia-induced ischaemic ECG Changes, Press. Med. 1994;23(2):78-9—Abstract.

Okin, Peter M. et al, "Electrocardiographic Repolarization Complexity and Abnormality Predict All-Cause and Cardiovascular Mortality in Diabetes The Strong Heart Study," Diabetes 53:434-440, 2004.

Peterson, Karl-Georg et al., "Regulation of Serum Potassium During Insulin-Induced Hypoglycemia," Diabetes. Jul. 1982;31:615-617.

Rana, Bushra S. et al, "Relation of QT Interval Dispersion to the Number Of Different Cardiac Abnormalities in Diabetes Mellitus," Am J Cardiol 2002;90:483-487.

Yanowitz, Frank G. MD, Prof. of Medicine, Univ. of Utah School of Medicine, "Lesson X. ST Segment Abnormalities," The Alan E. Lindsay—ECG Learning Center—In Cyberspace, 5 pages.

First Office Action, mailed Jan. 10, 2007: Related U.S. Appl. No. 11/043,780.

Notice of Allowance, mailed May 09, 2007: Related U.S. Appl. No. 11/043,780.

Notice of Allowance, mailed Mar. 07, 2007: Related U.S. Appl. No. 11/043,804.

NonFinal Office Action, mailed Jul. 14, 2008: Related U.S. Appl. No. 11/043,612.

NonFinal Office Action, mailed Jan. 23, 2008—Related U.S. Appl. No. 11/043,612.

NonFinal Office Action, mailed Sep. 10, 2008—Related U.S. Appl. No. 11/127,370.

Notice of Allowance, mailed Feb. 25, 2009—Related U.S. Appl. No. 11/127,370.

Eckert, Bodil et al. "*Hypoglycaemia Leads to an Increased QT Interval in Normal Men*," Clinical Physiology, vol. 18, No. 6 (1998), pp. 570-575.

Heller, Simon R, "*Abnormalities of the Electrocardiogram during Hypoglycemia: The Cause of the Dead in Bed Syndrome?*" Int. J. Clin. Pract. Suppl. No. 129 (Jul. 2002), pp. 27-32.

Robinson, R.T.C.E. et al. "*Changes in Cardiac Repolarization During Clinical Episodes of Nocturnal Hypoglycaemia in Adults with Type 1 Diabetes*," Diabetologia, vol. 47 (2004), pp. 312-315.

Jones, Timothy W. et al., "*Mild Hypolycemia and Impairment of Brain Stem and Cortical Evoked Potentials in Healthy Subjects*," Diabetes, vol. 39 (Dec. 1990), pp. 1550-1555.

* cited by examiner

SYSTEM AND METHOD FOR DETECTING HYPOGLYCEMIA BASED ON A PACED DEPOLARIZATION INTEGRAL USING AN IMPLANTABLE MEDICAL DEVICE

FIELD OF THE INVENTION

The invention generally relates to implantable medical devices such as pacemakers and implantable cardioverter/defibrillators (ICDs) and, in particular, to techniques for detecting hypoglycemia using such devices, especially within diabetics.

BACKGROUND OF THE INVENTION

Hypoglycemia (i.e. abnormally low blood glucose levels) is believed to be the cause of death in about three percent of insulin-treated diabetic patients. The putative mechanism for death due to hypoglycemia is a hypoglycemia-induced prolongation of the QT interval of the intracardiac electrogram (IEGM), which increases the risk of malignant ventricular tachycardia. See, for example, Eckert et al., "Hypoglycemia Leads to an Increased QT Interval in Normal Men," Clinical Physiology. 1998. Volume 18, Issue 6, Page 570 and Heller, "Abnormalities of the Electrocardiogram during Hypoglycaemia: The Cause of the Dead in Bed Syndrome," Int. J. Clin. Pract. Suppl. 2002 July; (129): 27-32. Note that QT interval represents the portion of the IEGM between the beginning of ventricular depolarization and the end of ventricular repolarization. Ventricular depolarization is manifest within the IEGM as a QRS complex (also referred to as an R-wave.) The QRS complex usually follows an atrial depolarization (also referred to as a P-wave.) Ventricular repolarization is manifest within the IEGM as a T-wave. Strictly speaking, P-waves, R-waves and T-waves are features of a surface electrocardiogram (ECG). For convenience and generality, the terms R-wave, T-wave and P-wave are used herein (and in the literature) to refer to the corresponding internal signal components as well.

In adults, if not treated properly, severe hypoglycemia may result in coma and irreversible brain damage. McCarthy et al., "Mild hypoglycemia and impairment of brain stem and cortical evoked potentials in healthy subjects." Department of Pediatrics, Yale University School of Medicine, New Haven, Conn. 06510.

Even in cases where hypoglycemia does not cause severe consequences, it is often the limiting factor in achieving good glycemic control in patients with diabetes, particular insulin-depended diabetics. In this regard, patients sometimes refrain from taking prescribed dosages of insulin for fear that the insulin might trigger an episode of hypoglycemia, which can be unpleasant. Failure to take the prescribed insulin prevents the patient from maintaining glycemic levels within a healthy range, thus often leading to additional health problems.

Hypoglycemia is also a serious and frequent problem in patients suffering hyperinsulinism, wherein the body generates too much insulin, thereby triggering episodes of hypoglycemia even if an otherwise sufficient amount of sugar or other glucose-generating substances are ingested. Medications appropriate for addressing hyperinsulinism includes sulfonylureas, meglitinides, biguanides, thiazolidinediones, or alpha glucosidase inhibitors.

In view of the adverse consequences of hypoglycemia, particularly within insulin-dependent diabetic patients, it is highly desirable to provide techniques for detecting hypoglycemia within such patients and automatically delivering appropriate therapy or warning signals. It is known that hypoglycemia can be detected based on observation of changes in the QT interval observed within an ECG, as well as based on observation of dispersion of QT intervals within the ECG (based on studies involving experimental hypoglycemia within adults with type 1 diabetes, i.e. diabetes wherein the body does not make insulin or at least doe not make enough insulin.) Studies in diabetics have also shown that hypoglycemia can be detected based on observation of a significant lengthening of the QTc interval occurring during spontaneous nocturnal hypoglycemia. See, Robinson et al., "Changes In Cardiac Repolarization During Clinical Episodes Of Nocturnal Hypoglycaemia In Adults With Type 1 Diabetes" Diabetologia. 2004 February;47(2):312-5. Epub 2004 Jan. 08. The QTc interval is an adjusted version of the QT interval that has been corrected to a heart rate of 60 beats per minute (bpm). See, also, U.S. Pat. No. 6,572,542 to Houben, et al., entitled "System and Method for Monitoring and Controlling the Glycemic State of A Patient," which describes a technique exploiting a combination of ECG signals and electroencephalogram (EEG) for the detection of hypoglycemia.

Accordingly, various techniques have been developed for detecting hypoglycemia based on ECG signals. However, it would also be desirable to provide techniques for detecting hypoglycemia based on IEGM signals so that detection may be performed by an implantable medical device without requiring surface electrodes. In particular, it is desirable to provide techniques for detecting hypoglycemia (or for detecting blood glucose levels so that hypoglycemia may be detected therefrom) for use with pacemakers or ICDs, as many patients at risk of hypoglycemia are also candidates for pacemakers and/or ICDs and such devices routinely detect the IEGM for use in pacing the heart and detecting arrhythmias One effective technique for detecting blood glucose levels based on IEGM signals sensed by an implantable medical device is set forth in U.S. Patent Application Serial No. 2004/0077962 of Kroll, published Apr. 22, 2004, entitled "System and Method for Monitoring Blood Glucose Levels Using an Implantable Medical Device." Briefly, with the technique of Kroll, blood glucose levels are determined by an implantable device based on IEGM signals by detecting and examine a combination of T-wave amplitude fraction and QTc interval. The technique may also be used to detect hypoglycemia based on changes in blood glucose levels. See also U.S. Pat. No. 5,741,211 to Renirie, entitled "System And Method For Continuous Monitoring Of Diabetes-Related Blood Constituents." Renirie is primarily directed to a Holter-type external monitor, but has some speculative discussions pertaining to implantable devices as well.

Another effective technique for use with implantable devices is set forth in U.S. patent application Serial No. 11/043,612, of Kil et al., filed Jan. 25, 2005, now U.S. Pat. No. 7,502,644 entitled "System And Method For Distinguishing Among Cardiac Ischemia, Hypoglycemia And Hyperglycemia Using An Implantable Medical Device". Briefly, techniques are described therein for detecting and distinguishing ischemia, hypoglycemia and hyperglycemia based on IEGM signals. Ischemia is detected based on a shortening of the interval between the QRS complex and the end of a T-wave (QTmax), alone or in combination with a change in ST segment elevation, which is the relative elevation of the portion of the cardiac signal between the end of the QRS-complex and the beginning of the T-wave. Alternatively, ischemia is detected based on a change in ST segment elevation combined with minimal change in the interval between the QRS complex and the end of the T-wave (QTend). Hypoglycemia is detected based on a change in ST segment elevation along with a lengthening of either QTmax or QTend. Hyperglycemia is detected based on a change in ST segment elevation along with minimal change in QTmax and in QTend. By exploiting QTmax and QTend in combination with ST segment elevation, changes in ST segment elevation caused by hypo/hyperglycemia can be properly distinguished from changes caused by ischemia.

Although the techniques of Kroll and Kil et al. are effective, it would be desirable to provide still other techniques for detecting hypoglycemia using an implantable device and it is to that end that aspects of the present invention are directed. It is particularly important to provide techniques for detecting hypoglycemia during paced beats rather than sensed beats as many patients with diabetes also have cardiac abnormalities requiring frequent pacing. Techniques based on an examination of the QRS complex are typically not effective in the case of paced beats since the QRS complex is replaced with an evoked response having a generally different shape. Accordingly, aspects of the invention are also directed to providing techniques for detecting hypoglycemia based on paced beats. Moreover, still other aspects of the invention are directed to providing techniques for tracking changes in glycemic state so as to allow patients to achieve improved glycemic control. In particular, it is desirable to provide techniques for predicting the onset of an episode of hypoglycemia in advance so as to warn the patient and still other aspects of the invention are directed to that end.

SUMMARY

In accordance with one illustrative embodiment, techniques are provided for use with an implantable medical device for detecting hypoglycemia. Broadly, the device tracks changes in a parameter representative of the energy associated with electrical cardiac signals corresponding to ventricular evoked responses (VERs), and then detects an episode of hypoglycemia based on the parameter. In one example, the parameter is a paced depolarization integral (PDI), which is calculated based on each VER. Changes in average PDI are tracked. Any significant increase in PDI over a relatively short period of time (e.g. between one and ten minutes) is deemed to be indicative of the onset of an episode of hypoglycemia. By tracking relatively short term increases in PDI, any long term increases in PDI due to other factors, such as chronic changes in the condition of the heart, are not used to detect hypoglycemia. Preferably, the period of time is at least one minute so that any beat-by-beat changes in PDI attributable to breathing modulation are averaged out.

Upon detecting hypoglycemia, appropriate warning signals are generated, which may include perceptible signals applied to subcutaneous tissue or short range telemetry warning signals transmitted to a device external to the patient, such as a bedside monitor. In one example, once a subcutaneous warning signal is perceived, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal. Upon confirmation of the warning, the patient then takes appropriate actions, such as ingesting foods suitable for increasing blood glucose levels or taking prescribed medications, if appropriate.

Certain therapies automatically provided by the implantable device may also be initiated or modified in response to hypoglycemia. If the patient is an insulin-dependent diabetic and the implantable device is equipped with a drug pump capable of delivering insulin directly into the bloodstream, insulin delivery by the pump is automatically suspended until blood glucose levels return to acceptable levels. If the patient suffers hyperinsulanism and if the drug pump is equipped to deliver medications appropriate to hyperinsulinism, delivery of such medications is titrated in response to hypoglycemia. In addition, if the device is an ICD, it may be controlled to begin charging defibrillation capacitors upon detection of hypoglycemia so as to permit prompt delivery of a defibrillation shock, which may be needed if hypoglycemia triggers VF due to a prolongation of the QT intervals. Additionally, or in the alternative, data representative of episodes of hypoglycemia or PDI trend information may be stored for subsequent physician review, such as date/time and duration of the episode, the individual PDI values detected, and any therapies automatically delivered. Trend information allows the patient and physician to develop and implement strategies for achieving better glycemic control within the patient.

Also, preferably, the recorded information is used to predict episodes of hypoglycemia so that warning signals may be generated to alert the patient to take appropriate action to prevent the episode from occurring. In one example, the prediction is performed by identifying a trend in increasing PDI. For example, if the recorded data indicates that the patient frequently has episodes of hypoglycemia early in the morning and PDI levels are found to be increasing early on a particular morning, then a warning signal is issued notifying the patient that an episode of hypoglycemia is likely.

Hence, improved techniques are provided both for reliably detecting hypoglycemia. The techniques are preferably performed by the implanted medical device itself so as to provide prompt warnings of hypoglycemia. Alternatively, the techniques may be performed by external devices, such as bedside monitors or the like, based on IEGM signals detected by an implanted device and transmitted to the external device. The techniques may be combined with other glycemic state prediction techniques, such as QT interval-based techniques or QRS-amplitude-based techniques to provide further specificity.

BRIEF DESCRIPTION OF THE DRAWINGS

Further features and advantages of the invention may be more readily understood by reference to the following description taken in conjunction with the accompanying drawings, in which: Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Overview of Implantable System

Figure 1:
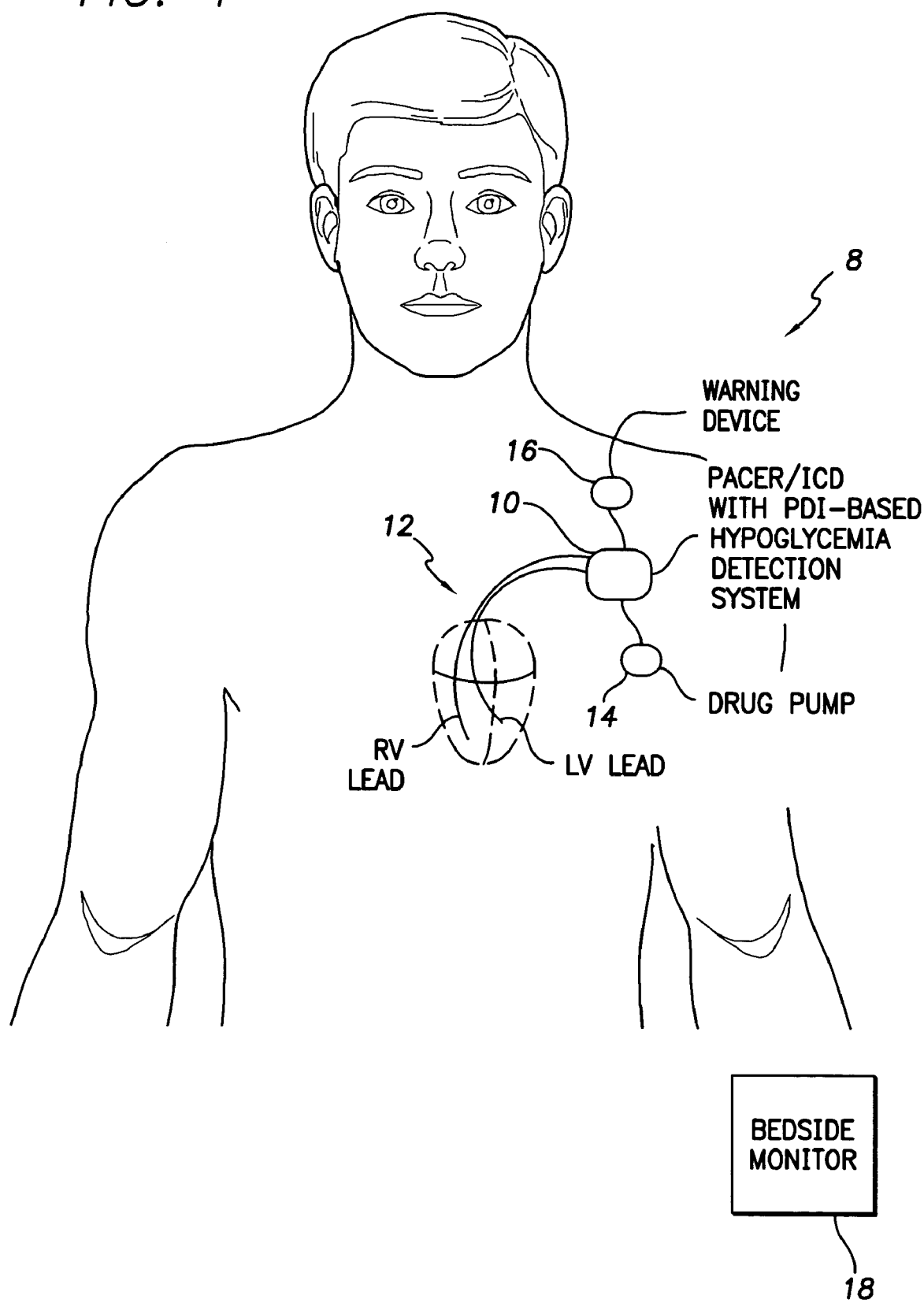
FIG. 1 illustrates pertinent components of an implantable hypoglycemia-responsive medical system having a pacemaker or ICD equipped to detect hypoglycemia within the patient based on a change in PDI and also equipped to control delivery of therapy and warning signals in response thereto.
Figure 7:
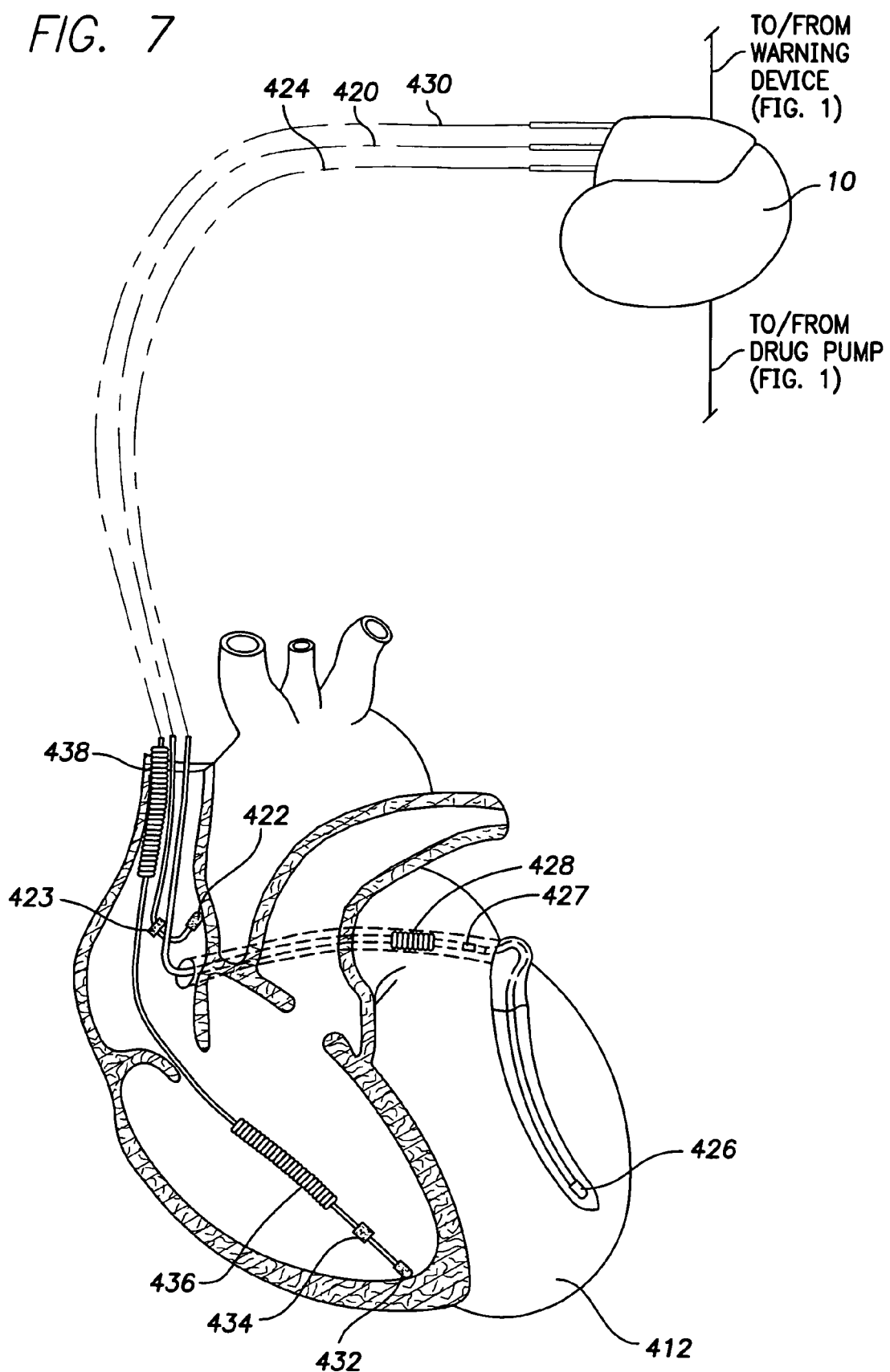
FIG. 7 is a simplified, partly cutaway view, illustrating the pacer/ICD of FIG. 1 along with at full set of leads implanted in the heart of the patient.

FIG. 1 provides a stylized representation of an implantable medical system 8 capable of: detecting hypoglycemia in a patient in which it is implanted and delivering appropriate warnings or insulin therapy. System 8 includes a pacer/ICD 10 or other cardiac stimulation device that incorporates internal components, shown individually in FIG. 8, for detecting and/or predicting hypoglycemia based on PDI derived from electrical cardiac signals sensed via a set of leads 12. (In FIG. 1, only exemplary RV and LV leads are shown. A full set of pacing leads and their respective electrodes is illustrated in FIG. 7.) Briefly, the pacer/ICD calculates PDI for each paced heartbeat and tracks changes in PDI from beat to beat. A significant short term decrease in PDI is indicative of the onset of hypoglycemia (e.g. average of PDI over 100 beats). If hypoglycemia is detected, therapy provided by the implanted system is controlled accordingly. In one example, if insulin is automatically delivered via an implanted insulin pump, insulin delivery is suspended. Additionally, or in the alternative, warning signals may be delivered to warn the patient, using either an internal warning device 16 or an external bedside monitor 18. Internal warning device 16 may be a vibrating device or a "tickle" voltage device that, in either case, provides perceptible stimulation to the patient to alert the patient so that the patient may take a dose of insulin or other appropriate medication. The bedside monitor provides audible or visual alarm signals to alert the patient, as well as textual or graphic displays.

Implantable drug pumps are discussed in U.S. Pat. No. 5,328,460 to Lord, et al., entitled "Implantable Medication Infusion Pump Including Self-Contained Acoustic Fault Detection Apparatus". Lord et al. also discusses implantable "tickle" warning devices. The bedside monitor may be directly networked with a centralized computing system for immediately notifying the physician as well. A system incorporating bedside monitoring units connected to a centralized external programmer system is described in U.S. Pat. No. 6,622,045 to Snell et al., "System and Method for Remote Programming of Implantable Cardiac Stimulation Devices." In addition, diagnostic information pertaining to hypoglycemia is transferred to the bedside monitor or is stored within the pacer/ICD for subsequent transmission to an external programmer (not shown in FIG. 1) for review by a physician or other medial professional. The physician may then prescribe any other appropriate therapies to address hypoglycemia. The physician may also adjust the operation of the pacer/ICD to activate, deactivate or otherwise control any therapies that are automatically applied. If located within a hospital, nursing home or the like, the bedside monitor may be directly networked with a centralized computing system for immediately notifying the staff of the onset of hypoglycemia within the patient. Additionally, if the implanted device is an ICD and the episode of hypoglycemia is sufficiently severe, the ICD automatically charges a defibrillation capacitor so that, should the hypoglycemia trigger ventricular fibrillation, a defibrillation shock can be given promptly. Preferably, in addition to the aforementioned hypoglycemia-responsive functions, the device is capable of performing a wide range of other cardiac rhythm management functions and for delivering a wide range of other forms of electrical cardiac therapy. This is discussed below with reference to FIG. 8.

Insofar as hypoglycemia prediction is concerned, the pacer/ICD includes components for analyzing trends in PDI data to identify periods in time when it is statistically likely that an episode of hypoglycemia will occur and to issue warning signals in advance thereof. For example, if trend data indicates that the patient frequently has an episode of hypoglycemia early in the morning and data detected during a particular morning indicates that PDI is beginning to increase, then a prediction is made by the pacer/ICD that there is a statistical likelihood that an episode of hypoglycemia is imminent and warnings are issued. Trend data may also be used by the physician and patient to aid in the developing a strategy for maintaining glycemic control by, for example, determining the optimal times during the day to eat meals or to take insulin. Also, the rate of change of mean PDI and the dynamics of separately obtained glucose and insulin profiles may be exploited to identify specific ailments. Otherwise conventional predictive techniques may be applied by the pacer/ICD to the PDI trend data to make the predictions.

Hence, FIG. 1 provides an overview of an implantable system capable of detecting hypoglycemia and delivering appropriate warnings or therapy. Embodiments may be implemented that do not necessarily perform all of these functions. For example, embodiments may be implemented that provide only for detecting hypoglycemia using the techniques of the invention and for warning the patient. Systems provided in accordance with the invention need not include all of the components shown in FIG. 1. Insulin pumps and implantable warning devices are not necessarily implanted. Other implementations may employ an external monitor for generating warning signals but no internal warning device. These are just a few exemplary embodiments. No attempt is made herein to describe all possible combinations of components that may be provided in accordance with the general principles of the invention. In addition, the particular locations of the implanted components shown in FIG. 1 are merely illustrative and may not necessarily correspond to actual implant locations.

Hypoglycemia Detection Technique

Figure 2:
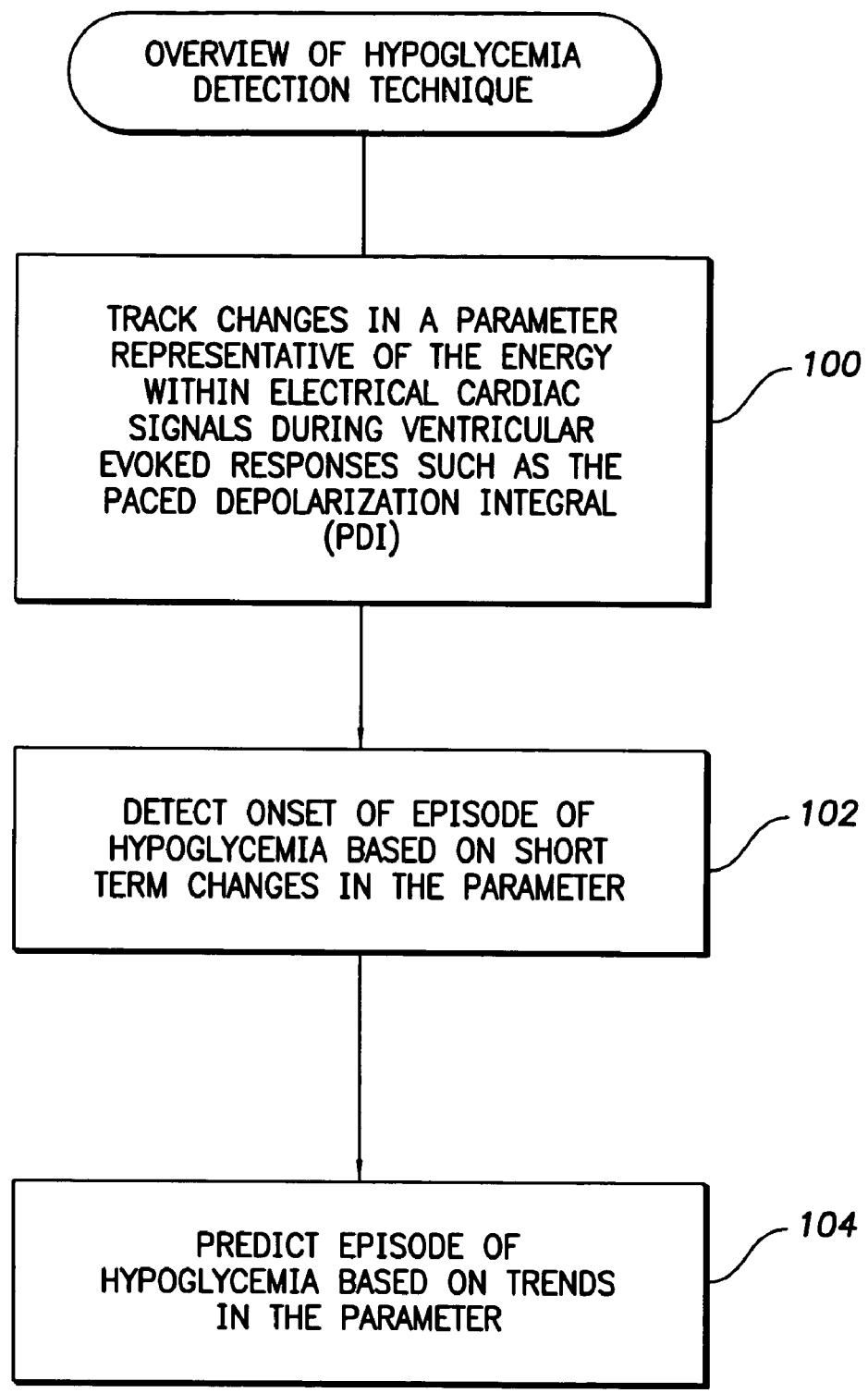
FIG. 2 is a flow diagram providing an overview of a general method for detecting hypoglycemia, which may be performed by the system of FIG. 1.

FIG. 2 summarizes the general method of the invention for detecting hypoglycemia within a patient. The method may be performed by the system of FIG. 1 or by any other suitably equipped implantable system. At step 100, the pacer/ICD tracks changes in PDI (or in other parameters representative of the energy within electrical cardiac signals during ventricular evoked responses.) Then, at step 102, the pacer/ICD detects the onset of an episode of hypoglycemia based on certain changes in the PDI, particularly a significant increase in PDI over a relatively short interval of time such as one to ten minutes. At step 104, the pacer/ICD analyzes the changes in PDI to detect any trends therein and predicts the onset of an episode of hypoglycemia based on the trends. In other words, the pacer/ICD is capable both of detecting an episode of hypoglycemia as it occurs (step 102) and of also predicting an episode before it occurs (step 104).

Figure 3:
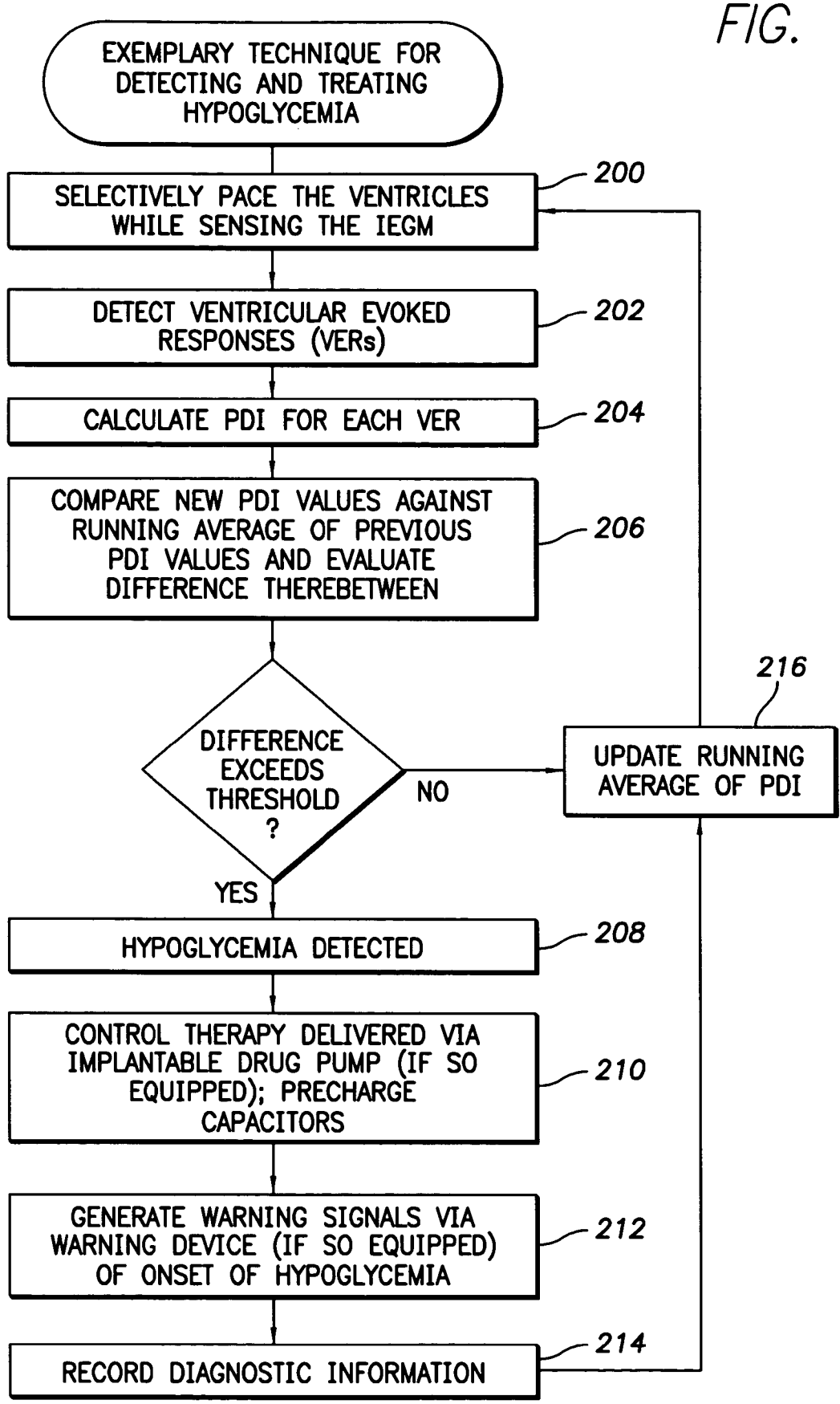
FIG. 3 is a flow diagram illustrating an exemplary technique performed in accordance with the general method of FIG. 2 for controlling delivery of therapy and warning signals in response to hypoglycemia.

FIG. 3 provides a more detailed example of hypoglycemia detection. Beginning at step 200, the pacer/ICD selectively paces in the ventricles of patient while sensing the IEGM. At step 202, ventricular evoked responses (VERs) are detected. At step 204, the PDI for each VER is calculated. For a complete description of PDI, also known as the ventricular depolarization gradient, see U.S. Pat. No. 4,759,366 to Callaghan, entitled "Rate responsive pacing using the ventricular gradient." Techniques for calculating PDI are also discussed in U.S. Pat. No. 6,731,985 to Poore, et al., entitled "Implantable Cardiac Stimulation System and Method for Automatic Capture Verification Calibration." At step 206, the newly detected PDI values are compared against a running average of previous PDI values (or against any suitable representation of nominal PDI values for the patient) to detect and evaluate and any recent change. If the difference between the PDI values and the running average exceeds some predetermined threshold, hypoglycemia is thereby detected, at step 208. Depending upon the particular implementation, some predetermined number of individual PDI values may need to each exceed the predetermined threshold before hypoglycemia is detected. This prevents a single aberrant PDI value from triggering hypoglycemia therapy. Alternatively, an average of the most recent PDI values must exceed the threshold, such as an average of all PDI values detected over the last 60 seconds or an average of the last 100 consecutive beats.

Otherwise routine experimentation may be performed to determine an optimal threshold value for use in detecting hypoglycemia. The threshold values may vary from patient to patient and may be programmed or adjusted by a physician via an external programming device. In still other implementations, rather than detecting hypoglycemia by comparing new PDI values against a running average of PDI values, the new PDI values may be compared against a fixed threshold. As can be appreciated, a wide variety of threshold-based techniques may be employed for detecting hypoglycemia based upon the newly detected PDI values. FIG. 3 merely illustrates one example.

The detection of hypoglycemia made at step 206 may be corroborated using other hypoglycemia detection techniques including those set forth in the aforementioned patent applications of techniques of Kroll and Kil et al. as well as QT interval-based techniques.

Within steps 210-214, the pacer/ICD responds to the newly detected episode of hypoglycemia. The specific response depends upon the capabilities of the implanted system and the needs of the particular patient. If insulin is being automatically delivered to an insulin-dependent diabetic via an implantable drug pump then, at step 210, delivery of insulin is suspended so as to prevent additional insulin from exacerbating the hypoglycemia. On the other hand, if the patient has been diagnosed with hyperinsulinism, delivery of appropriate medications such as sulfonylureas, meglitinides, biguanides, thiazolidinediones, or alpha glucosidase inhibitors, may be initiated using an implantable drug pump (assuming such drugs are suitable for automatic delivery via a drug pump.) Preferably, any hypoglycemia-related conditions of the patient are diagnosed in advance by the physician and the resulting diagnosis is programmed into the implanted pacer/ICD by the physician for use in controlling therapy. At step 214, the pacer/ICD also preferably begins charging its defibrillation capacitors in expectation of delivery of shocks in the event that the episode of hypoglycemia triggers ventricular fibrillation. At step 212, appropriate warning signals are generated via an implanted warning device or external bedside monitor. Such warning signals are particularly desirable within implantable systems not equipped to provide any automatic hypoglycemia therapy. For example, if patient suffers hyperinsulinism, but no implantable drug pump is provided for delivering suitable medications internally, then warning signals are provided to alert the patient to manually take the medications. If patient is an insulin-dependent diabetic, then warning signals are provided to alert the patient to take a suitable number of sugar pills or other substances or medications sufficient increase blood glucose levels.

Preferably, the warning signals are of sufficient magnitude to awaken the patient, if sleeping. The magnitude of the warning signals may be controlled based upon the time of day or the activity state of the patient so as to be of greater magnitude if the patient appears to be resting or sleeping. Otherwise conventional sleep detectors may also be employed in this regard. In one example, once a subcutaneous warning signal is perceived, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal. Upon confirmation of the warning, the patient then takes appropriate actions, such as ingesting foods suitable for increasing blood glucose levels or taking prescribed medications, if appropriate. Warning devices of this type are discussed in U.S. patent application Ser. No. 10/603,429, of Wang et al., entitled "System and Method for Detecting Cardiac Ischemia Using an Implantable Medical Device." Also, preferably, any warning signals transmitted to a bedside monitor are then conveyed to medical personal via any suitable communication network, particularly if the patient is in a hospital, rest home or the like where medical personnel can easily summoned.

Note that the charging of capacitors at step 210 may be performed, depending on the implementation, only if previously delivered warning signals failed to alert the patient to take steps to terminate the episode of hypoglycemia. For example, if the episode of hypoglycemia continues for some predetermined period of time despite the delivery of warning signals, then, and only then, are the capacitors pre-charged. Changes in cardiac pacing therapy may be appropriate was well.

At step 214, appropriate diagnostic information is recorded, such as the date/time of the episode of hypoglycemia and its severity, as quantified by the detected PDI values.

Then, at step 216, the running average is updated, before processing returns to step 200 further pacing of the ventricles. Note that, following step 206, if the difference between new PDI values and the running average does not exceed the predetermined threshold, hypoglycemia is not detected and so step 216 is simply performed to update the running average.

Figure 4:
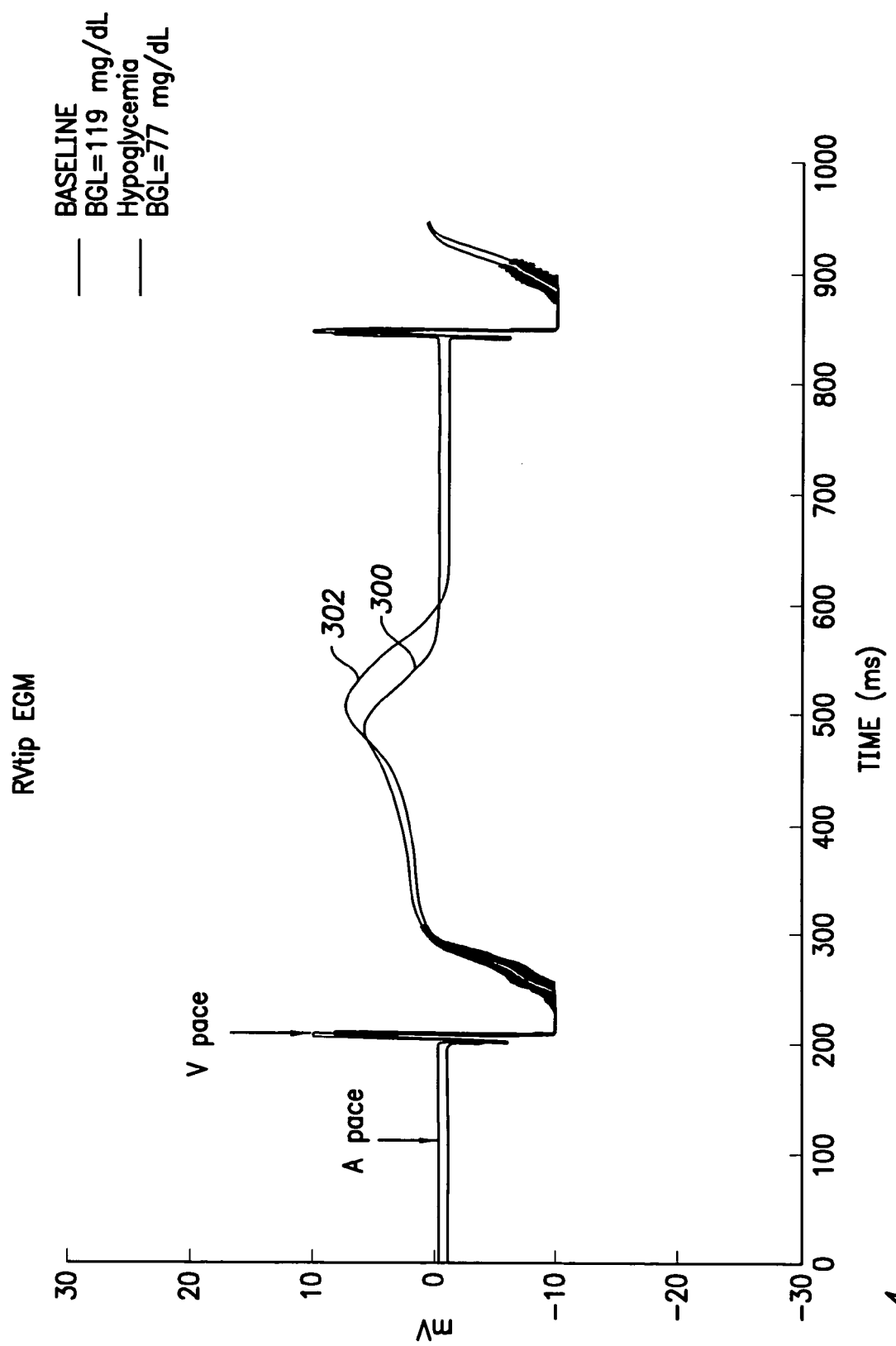
FIG. 4 is a graph illustrating heartbeats obtained from a canine test subject superimposed on one another and particularly illustrating differences in the morphology of the heartbeats due to blood glucose levels.

FIG. 4 illustrates the effect that hypoglycemia has on the morphology of IEGM signals that is exploited by the technique of FIG. 3. In FIG. 4, a first trace 300 illustrates the shape of an IEGM signal for a canine test subject in which blood glucose levels are normal. The trace illustrates several individual cardiac signals superimposed one on the other. The IEGM signals correspond to paced atrial and ventricular events. A-pace and V-pace events are identified. In the example, the blood glucose level is 119 milligrams per deciliter (mg/dL.) This represents a baseline value. Trace 302 illustrates the shape of the IEGM for the test subject once hypoglycemia has occurred. Again, the trace illustrates several cardiac signals superimposed one on the other. In the example, the blood glucose level is only 77 mg/dL. As can be seen, there is a significant difference in the morphology of the IEGM signals depending upon the blood glucose level. During hypoglycemia, the T-wave has a greater amplitude and the peak of the T-wave is delayed, i.e. the QT interval becomes prolonged. As noted above in the Summary, prolongation of the QT segment can result in malignant tachyarrhythmias, including ventricular fibrillation. In any case, the change in the morphology of the IEGM signals subsequent to the ventricular pacing pulse results in a change in PDI.

Figure 5:
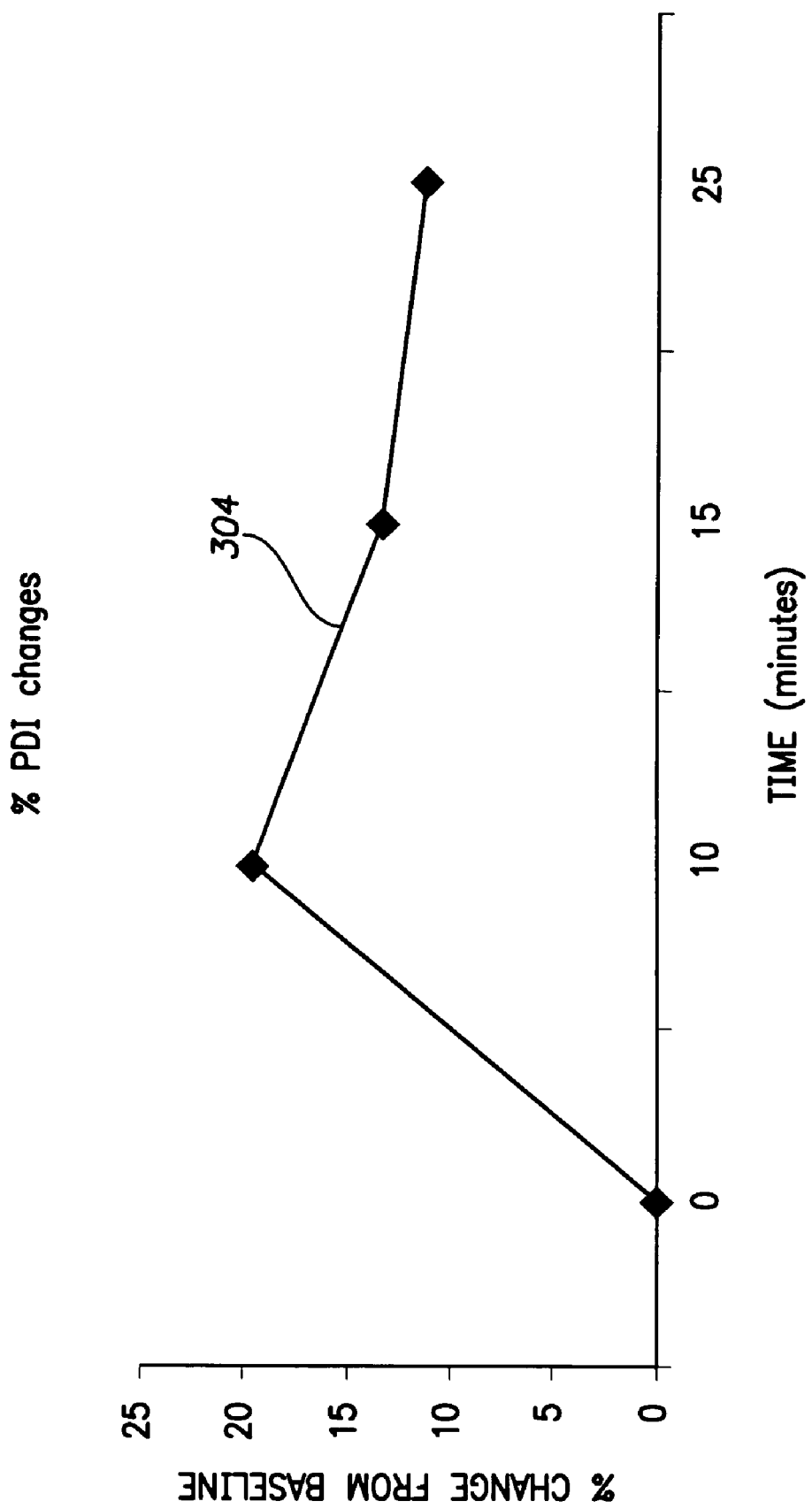
FIG. 5 is a graph illustrating PDI as a function of time obtained from a canine test subject and particularly illustrating changes in PDI levels due to changes in blood glucose levels.

FIG. 5 provides a graph 304 illustrating the percentage change in mean PDI as a function of time from a baseline blood glucose level. In the example of FIG. 5, a bolus of insulin was injected into a canine test subject, triggering a significant increase (up to about 20%) in the mean PDI over the baseline value due to the drop in blood glucose levels. Although not shown in FIG. 5, the blood glucose levels for the test subject began to drop promptly after injection of the insulin. The actual episode of hypoglycemia did not begin until the blood glucose levels dropped below minimum acceptable glycemic levels. However, mean PDI began to change almost immediately in accordance with the drop in blood glucose levels. In other words, a detectable change in mean PDI can occur even before an episode of hypoglycemia actually begins, thus allowing for prediction of the episode and allowing for an early warning to be issued to the patient.

Figure 6:
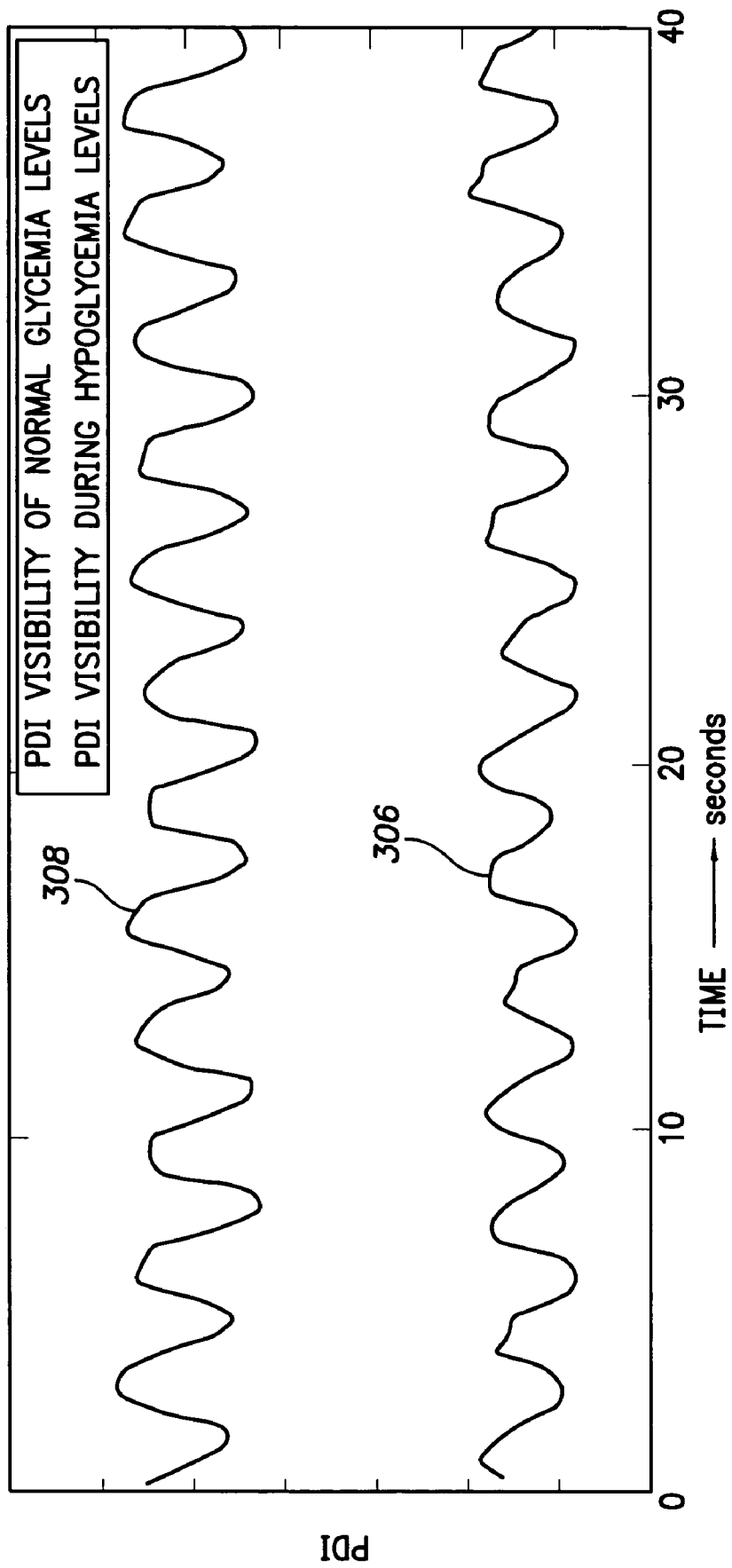
FIG. 6 is a graph illustrating PDI as a function of time obtained from a canine test subject and particularly illustrating modulation of PDI levels due to respiration.

Thus FIG. 5 illustrates changes in mean PDI caused by changes in blood glucose levels. PDI also varies cyclically due to respiration. This is illustrated in FIG. 6, which provides graphs illustrating PDI values (shown on an arbitrary scale) varying with time derived from a ventricular unipolar lead over a period of about 40 seconds from a canine test subject. Graph 306 illustrates PDI obtained at a normal glycemic levels; whereas graph 308 illustrates PDI obtained at a hypoglycemic levels. As can be seen, the PDI values are modulated by respiration. However, a mean level of PDI of graph 308 (during hypoglycemia) is considerably higher than a mean level of PDI of graph 306 (without hypoglycemia.) As noted above, by examining PDI over a period of (typically) at least one minute, modulation due to respiration can be averaged out.

What have been described are various techniques for detecting hypoglycemia and controlling therapy in response thereto. For the sake of completeness, a detailed description of an exemplary pacer/ICD will now be provided. However, principles of invention may be implemented within other pacer/ICD implementations or within other implantable devices. In particular, techniques of the invention can be implemented as a subcutaneous monitor, which is particularly advantageous for type 1 diabetics.

Exemplary Pacer/ICD

Figure 8:
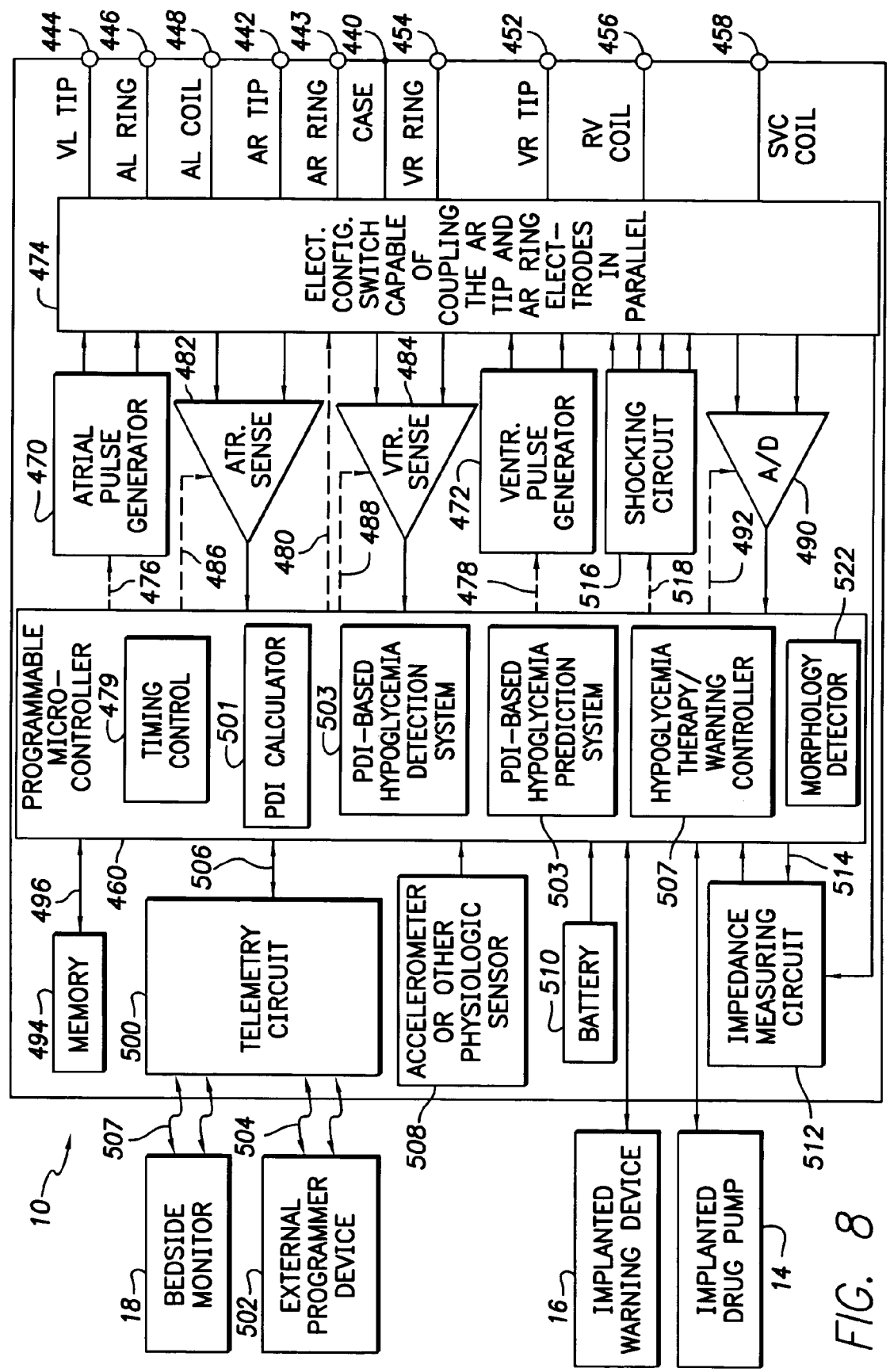
FIG. 8 is a functional block diagram of the pacer/ICD of FIG. 7, illustrating basic circuit elements that provide cardioversion, defibrillation and/or pacing stimulation in the heart and particularly illustrating components for detecting hypoglycemia and for controlling therapy and warnings in response thereto.

With reference to FIGS. 7 and 8, a description of an exemplary pacer/ICD will now be provided. FIG. 7 provides a simplified block diagram of the pacer/ICD, which is a dual-chamber stimulation device capable of treating both fast and slow arrhythmias with stimulation therapy, including cardioversion, defibrillation, and pacing stimulation as well as providing for the aforementioned hypoglycemia detection and therapy. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS as for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 7, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 410 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned hypoglycemia detection and therapy.

The housing 440 for pacer/ICD 410, shown schematically in FIG. 8, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 8, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. In addition, the switch includes components for selectively coupling the atrial tip and ring electrodes in parallel during an AF risk assessment procedure.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 8. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 8, pacer/ICD 410 is shown as having an impedance measuring circuit 512 which is enabled by the microcontroller 460 via a control signal 514. Thoracic impedance may be detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Insofar as hypoglycemia detection and therapy is concerned, the microcontroller includes a PDI calculator 501 for calculating PDI. A PDI-based hypoglycemia detection system 503 detects an ongoing episode of hypoglycemia using the techniques discussed above. A PDI-based hypoglycemia prediction system 505 predicts the onset of an episode of hypoglycemia using the techniques discussed above. A hypoglycemia therapy/warning controller 507 controls delivery of therapy and warning signals in accordance with the techniques discussed above.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for use with an implantable medical device for detecting hypoglycemia in a patient in which the device is implanted, the method comprising:

detecting electrical cardiac signals corresponding to ventricular evoked responses; and detecting an episode of hypoglycemia based on changes in a parameter representative of the energy associated with the electrical cardiac signals corresponding to ventricular evoked responses;

wherein the parameter incorporates an integral of portions of the electrical cardiac signals corresponding to ventricular evoked responses.

2. The method of claim 1 wherein the parameter is a paced depolarization integral (PDI).

3. The method of claim 1 wherein detecting an episode of hypoglycemia based on the parameter comprises detecting one or more of a significant increase in the parameter and a significant rate of change of a mean of the parameter.

4. The method of claim 3 wherein detecting a significant increase in the parameter is performed to detect an increase above a hypoglycemia detection threshold.

5. The method of claim 1 further comprising controlling therapy in response to the detection of an episode of hypoglycemia.

6. The method of claim 5 wherein an implantable drug pump is provided for delivering insulin and wherein controlling therapy in response to the detection of an episode of hypoglycemia comprises reducing insulin delivery to the patient using the insulin pump.

7. The method of claim 5 wherein an implantable drug pump is provided for delivering selected medications in response to hyperinsulinism and wherein controlling therapy in response to the detection of an episode of hypoglycemia comprises delivering the selected medications.

8. The method of claim 1 further comprising generating a warning signal in response to detection of an episode of hypoglycemia.

9. The method of claim 8 wherein an implantable warning device is provided and wherein generating a warning signal comprises delivering a perceptible warning signal to the patient via the implantable warning device.

10. The method of claim 8 wherein an external warning device is provided and wherein generating a warning signal comprises transmitting control signals to the external warning device for controlling the external device to generate warning signals.

11. The method of claim 1 wherein the implantable device includes a defibrillator with defibrillation shock capacitors and wherein the method further comprises charging the capacitors in response to detection of an episode of hypoglycemia.

12. The method of claim 1 further comprising recording diagnostic information representative of the parameter representative of the energy associated with electrical cardiac signals corresponding to ventricular evoked responses.

13. The method of claim 12 further comprising examining the recording diagnostic information to predict episodes of hypoglycemia.

14. The method of claim 13 wherein examining the recording diagnostic information to predict episodes of hypoglycemia is performed by identifying a trend in increasing PDI.

15. The method of claim 1 wherein detecting a parameter comprises tracking changes in the parameter over time.

16. A system for use with an implantable medical device for detecting hypoglycemia in a patient in which the device is implanted comprising:

means for detecting electrical cardiac signals corresponding to ventricular evoked responses; and means for detecting an episode of hypoglycemia based on changes in a parameter representative of the energy associated with the electrical cardiac signals corresponding to ventricular evoked responses;

wherein the parameter incorporates an integral of portions of the electrical cardiac signals corresponding to ventricular evoked responses.

* * * * *

UNITED STATES PATENT AND TRADEMARK OFFICE
CERTIFICATE OF CORRECTION

PATENT NO. : 7,590,443 B2  Page 1 of 1
APPLICATION NO. : 11/117624
DATED : September 15, 2009
INVENTOR(S) : Rupinder Bharmi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1115 days.

Signed and Sealed this

Twenty-first Day of September, 2010

David J. Kappos
*Director of the United States Patent and Trademark Office*